(12) United States Patent
Bartha

(10) Patent No.: US 8,632,507 B2
(45) Date of Patent: Jan. 21, 2014

(54) AUTO-INJECTOR

(75) Inventor: Istvan Bartha, Järfälla (SE)

(73) Assignee: SHL Group AB, Nacka Strand (SE)

( * ) Notice: Subject to any disclaimer, the term of this patent is extended or adjusted under 35 U.S.C. 154(b) by 545 days.

(21) Appl. No.: 12/867,006

(22) PCT Filed: Feb. 3, 2009

(86) PCT No.: PCT/EP2009/051202
§ 371 (c)(1),
(2), (4) Date: Oct. 26, 2010

(87) PCT Pub. No.: WO2009/101005
PCT Pub. Date: Aug. 20, 2009

(65) Prior Publication Data
US 2011/0034881 A1 Feb. 10, 2011

(30) Foreign Application Priority Data
Feb. 12, 2008 (SE) ........................... 0800313

(51) Int. Cl.
*A61M 5/00* (2006.01)
*A61M 5/315* (2006.01)

(52) U.S. Cl.
USPC ............ 604/211; 604/207; 604/208; 604/218

(58) Field of Classification Search
USPC ......... 604/181, 187, 207, 208, 209, 210, 211, 604/218, 246
See application file for complete search history.

(56) References Cited

U.S. PATENT DOCUMENTS

2004/0186431 A1* 9/2004 Graf et al. ............... 604/124

FOREIGN PATENT DOCUMENTS

EP    1218042 B1   7/2002
WO   2007/099044 A1   9/2007

OTHER PUBLICATIONS

EPO, Int'l Search Report in PCT/EP2009/051202, Jun. 17, 2009.
EPO, Written Opinion in PCT/EP2009/051202, Jun. 17, 2009.

* cited by examiner

*Primary Examiner* — Kevin C Sirmons
*Assistant Examiner* — Shefali Patel
(74) *Attorney, Agent, or Firm* — Piedmont IP PLLC

(57) ABSTRACT

An auto-injection device has a housing with a medicament container disposed within; a dose setting mechanism for setting a dose of a medicament; a drive nut and a plunger rod operably connected, with an energy accumulator operably connected to the dose setting mechanism; and an activating mechanism and a positioning mechanism operably connected to the plunger rod for locking the plunger rod from being displaced. The positioning mechanism includes a locking nut arranged to cooperate with fixed, flexible locking features for locking the locking nut from rotation. A resilient member arranged inside the plunger rod is configured to allow the plunger rod to be resiliently and axially displaced when the locking nut is unlocked.

11 Claims, 4 Drawing Sheets

AUTO-INJECTOR

TECHNICAL AREA

The present invention relates to an auto-injection device and in particular an auto-injector capable of automatically adjusting the plunger rod in relation to different medicament container sizes.

TECHNICAL BACKGROUND

Injectors with different types of automatic functions have been developed under a number of years. The functions could comprise penetration, injection, dose setting, mixing, priming, needle shields, just to mention a few.

One type of injectors is the one that is reusable, and/or capable of housing different sizes of medicament cartridges. In this aspect, and in particular when the injector should be capable to deliver a set dose, it is important that the plunger rod or the like acting on the cartridge for expelling a dose of medicament should be in the proper position in relation to the cartridge when the first dose is to be delivered from a new cartridge. This position should preferably be set automatically by the device, i.e. the user-actions should be kept to a minimum in order to minimize the risk of wrong handling of the device.

One such solution of automatically adjusting the position of the plunger rod in relation to a stopper of a medicament cartridge is disclosed in patent No. EP 1 218 042. It describes a medication delivery pen comprising a body wherein a threaded plunger rod or lead screw acting on a stopper of a medicament cartridge is arranged inside said body. The lead screw is provided with a spring at its proximal end for biasing the lead screw in the distal direction, i.e. towards the stopper. The lead screw and the spring are arranged inside a tubular driver. In this manner, when a medicament cartridge is inserted in a cartridge holder and mounted to the body, the lead screw is constantly pushed against the stopper until the cartridge holder is locked against the rest of the body, wherein the movement of the lead screw is also locked in the proper position in relation to the stopper. The device is thus "reset" and since there is no play between the lead screw and the stopper, the injector pen delivers the right, preset dose, from the first injection.

The design however requires that the pen injector becomes somewhat longer than without the spring, since it is arranged at the proximal end of the lead screw. Further, since the spring is held in place inside the driver, thereby preventing it from buckling or bulging, the lead screw has to have the corresponding diameter in order to fit inside the driver. The rather small diameter reduces the precision of the pitch of the threads, which in turn reduces the precision of the dose quantity delivered in relation to the preset dose.

There is thus room for improvements regarding automatic adjustment of drive units in relation to medicament cartridges in injectors.

BRIEF DESCRIPTION OF THE INVENTION

The aim of the present invention is to remedy the drawbacks of the state of the art. This aim is solved by the features of the independent patent claim. Preferable embodiments of the invention are the subject of the dependent claims.

According to a main aspect of the invention it is characterised by an auto-injection device having a front end and a rear end arranged to comprise a rear housing and a container housing, releasably connected to each other; a medicament container disposed within the container housing, wherein the container has a front opening with or for a delivery member for delivering the medicament therethrough and at least one movable stopper; a dose setting mechanism capable of setting and resetting a dose of medicament; a drive nut releasably connected to the dose setting mechanism; wherein said device further comprises a hollow plunger rod rotatably connected to said drive nut and arranged to have its front end in contact with said stopper; an energy accumulating member having a first end connected to the dose setting mechanism and a second end connected to a fix point of the rear housing, such that when said dose setting mechanism is operated to set a dose, said energy accumulating member accumulates energy in terms of at least one predetermined step; an activating mechanism releasably connected to said drive nut and capable of locking said drive nut against rotation when a dose is being set and of releasing said drive nut when said activating mechanism is manually activated such that said hollow plunger rod is linearly displaced towards the front end of the device by the rotation of said drive nut due to the energy accumulated in the energy accumulating member and transferred through the dose setting mechanism; a positioning mechanism operably connected to said hollow plunger rod and capable of locking said hollow plunger rod from being resiliently and axially displaced by rotation; wherein said positioning mechanism comprises a first locking nut rotationally locked but axially slidable surrounding said hollow plunger rod and arranged to co-operate with flexible locking means arranged on said rear housing for locking said first locking nut from rotation; and a resilient member arranged inside said hollow plunger rod capable of allowing said hollow plunger rod to be resiliently and axially displaced when said first locking nut is unlocked.

The advantage with the present invention is an auto-injector having both a dose setting and resetting function, and positioning mechanism having a resilient member that is completely covered inside the hollow plunger rod for automatically adjusting the position of the plunger rod in relation to the stopper. Thus the resilient member will not obstruct any other components or functions of the device. Further the device can be made shorter because the resilient member, since it is completely contained inside the hollow plunger rod. Therefore the resilient member does not add to the length of the injector.

Further, since the resilient member is arranged inside the hollow plunger rod, it is possible to choose any suitable diameter of the hollow plunger rod and thereby the precision of the dose delivered can be improved by a larger diameter.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
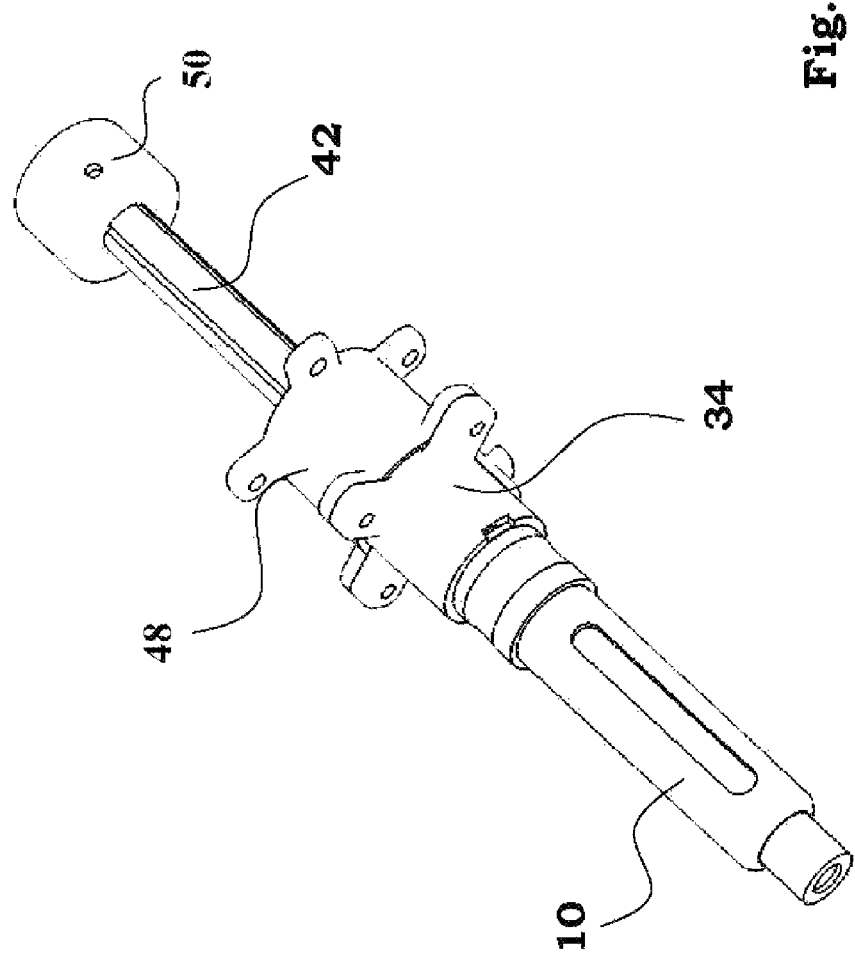
FIG. 1 is a perspective view of an embodiment of the present invention.
Figure 2:
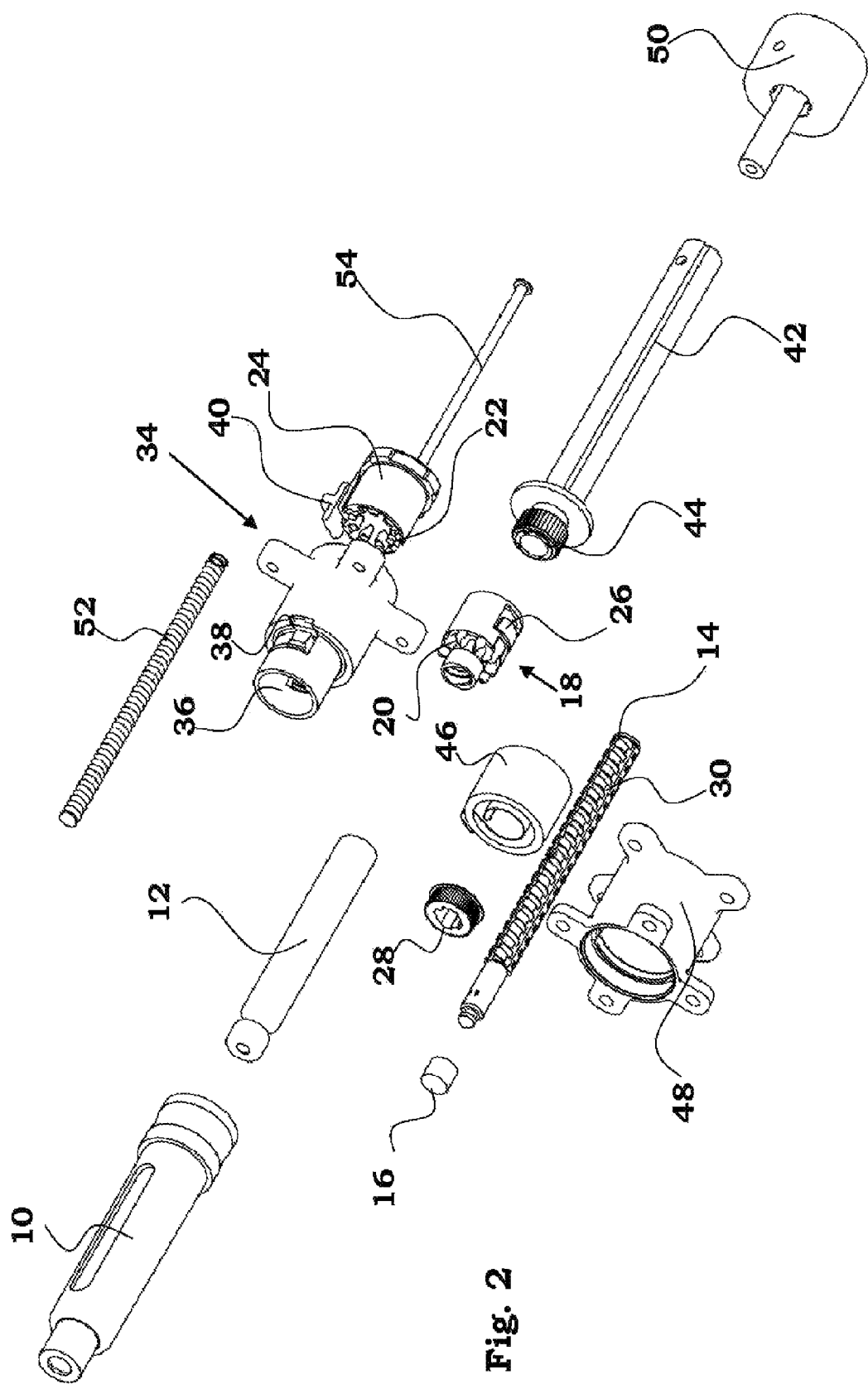
FIG. 2 is an exploded view of the embodiment of FIG. 1.

In the present application, when the term "rear part/end" is used, this refers to the part/end of the injection device, or the parts/ends of the members thereof, which under use of the injection device is located the furthest away from the medicament injection site of the patient. Correspondingly, when the term "front part/end" is used, this refers to the part/end of the injection device, or the parts/ends of the members thereof, which under use of the injection device is located closest to the medicament injection site of the patient.

The present invention relates to an auto-injection device having a front end and a rear end arranged to comprise a rear housing and a container housing 10 releasably connected to each other. In the embodiment shown in the figures, the rear housing comprising a first rear housing 34, a second rear housing 48, and a third rear housing. In the drawings, the third rear housing is removed for clarity. It must be observed that the rear housing may also be a two-piece housing or a one-piece housing. A medicament container 12, e.g. a cartridge, a syringe or the like, is disposed within the container housing, wherein the container has a front opening with or for a delivery member, e.g. a needle, for delivering the medicament therethrough and at least one movable stopper. The container housing having attachment means (not shown) on its outer circumference surface at its front end for attaching a delivery member, when the container is of the cartridge type. The device further comprises a dose setting mechanism capable of setting and resetting a dose of medicament; a drive nut 18 releasably connected to the dose setting mechanism; an energy accumulating member 46, e.g. a spirally wound leaf spring, having a first end connected to the dose setting mechanism and a second end connected to a fix point of the rear housing, such that when said dose setting mechanism is operated to set a dose, said energy accumulating member accumulates energy in terms of at least one predetermined step; a hollow plunger rod 14 rotatably connected to said drive nut and arranged to have its front end in contact with said stopper; an activating mechanism 24 releasably connected to said drive nut and capable of locking said drive nut against rotation when a dose is being set and of releasing said drive nut when said activating mechanism is manually activated such that said hollow plunger rod is linearly displaced towards the front end of the device by the rotation of the drive nut due to the energy accumulated in the energy accumulating member and transferred through the dose setting mechanism; a positioning mechanism operably connected to said hollow plunger rod and capable of locking said hollow plunger rod from being resiliently and axially displaced by rotation; wherein said positioning mechanism comprises a first locking nut 28 rotationally locked but axially slidable surrounding said hollow plunger rod and arranged to co-operate with flexible locking means 38 arranged on said rear housing for locking said first locking nut from rotation; and a resilient member 52 arranged inside said hollow plunger rod capable of allowing said hollow plunger rod to be resiliently and axially displaced when said first locking nut is unlocked for automatically adjusting the position of the plunger rod in relation to the stopper.

The hollow plunger rod 14 comprises a spinner 16 at its front end. The spinner, which is arranged for reducing the friction when the hollow plunger rod rotates, is arranged in contact with the stopper in the container. The drive nut 18 comprises a set of threads on its inner circumference surface that interfaces with a corresponding set of threads on the outer circumference surface of the hollow plunger rod. The drive nut further comprises a flexible engagement means 26 extending through a recess on its outer circumference surface, and wherein said flexible engagement means 26 comprises second radial inwardly protruding means. The hollow plunger rod further comprises elongated grooves 30 on its outer surface that interfaces with corresponding protrusions 32 on the inner circumference surface of the first locking nut, whereby the hollow plunger rod is rotationally locked to said first locking nut but axially slidable through said first locking nut.

The flexible locking means 38 are arranged on the front end 36 of the rear housing extending through a recess on the outer circumference surface of said front end 36, wherein said flexible locking means comprises first radial inwardly protruding means that interfaces with a corresponding first set of grooves arranged as a ratchet on the outer circumference surface of said first locking nut, such that when first radial inwardly protruding means are in contact with said corresponding first set of grooves, said first locking nut is rotationally locked.

The front part 36 of said rear housing is arranged with a set of engagements, e.g. threads, bayonet, on its outer circumference surface, wherein said set of engagements interfaces with a corresponding set of engagements arranged on the distal inner circumference surface of said container housing.

The dose setting mechanism comprises a dose knob 50 arranged to be rotated and placed at the rear end of the device, a drive shaft 42 surrounding said hollow plunger rod and operably connected to said dose knob, a second locking nut 44 attached to the front end of said drive shaft 42, wherein said second locking nut comprises a second set of grooves arranged as a ratchet on its outer circumference surface, wherein said second set of grooves interfaces with said second radial inwardly protruding means of said flexible engagement means 26, and wherein said second set of grooves and said protruding means of said flexible engagement means 26 comprises a geometry such that when a dose is set, the drive shaft is rotated in only one direction. Further, the first end of said energy accumulating member 46 is connected to the drive shaft.

The drive nut further comprises a first set of engagement means 20, e.g. teeth, on its outer circumference surface that interfaces with a corresponding second set of engagement means 22, e.g. teeth, on the inner circumference surface of said activating mechanism, such that said sets of engagement 20, 22 are arranged to be in contact with each other for locking said drive nut in a rotationally locked position when said energy accumulating member is tensioned via the drive shaft for accumulating energy.

The activating mechanism comprises a manually activated knob 40, which is arranged through a passage on the rear housing (not shown), such that when said manually activated knob is axially displaced, said second set of engagement means 22 are released from the first set of engagement means 20 whereby the energy accumulated in the energy accumulating member is transferred to the drive nut via the drive shaft and the second locking nut for allowing the drive nut to rotate and thereby allowing the hollow plunger rod to be axially and linearly driven towards the front end of the device.

The dose knob and the drive shaft are arranged to be axially displaced, such that the interfacing between the second set of grooves of said second locking nut and said second radial inwardly protruding means of said flexible engagement means 26, is forced out of engagement.

Figure 3:
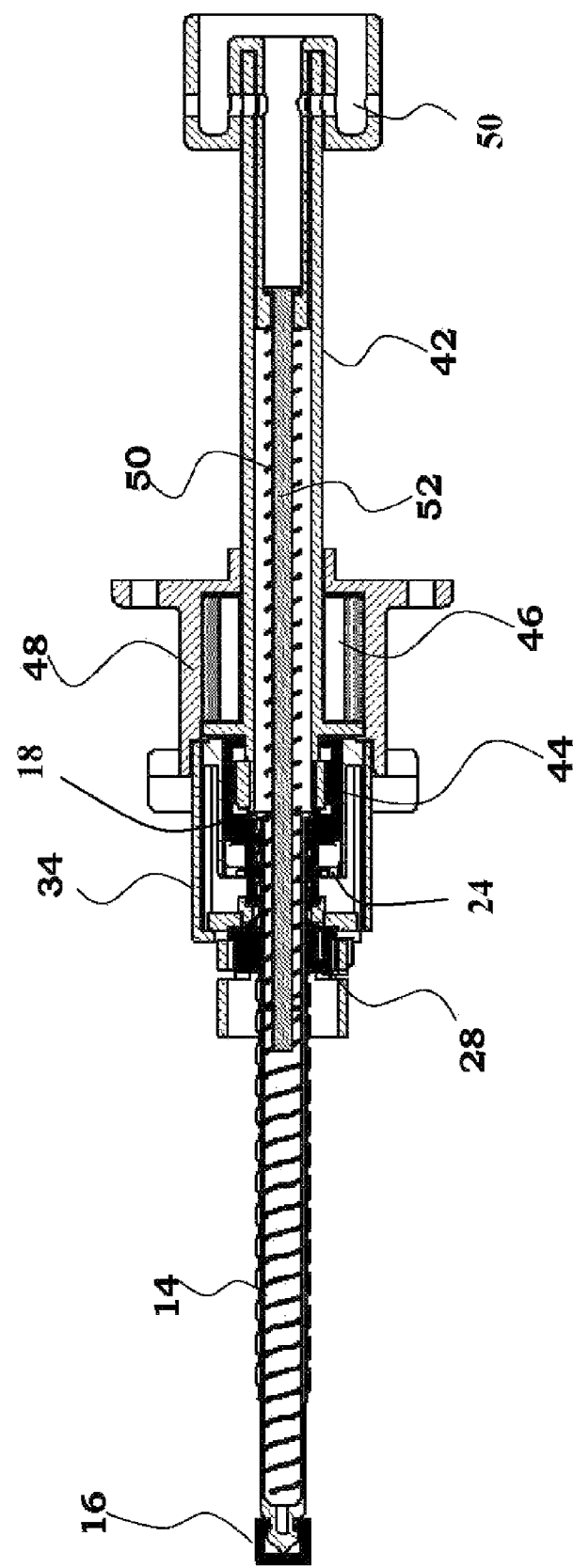
FIG. 3 is a cross-sectional view of the embodiment of FIG. 1.
Figure 4:
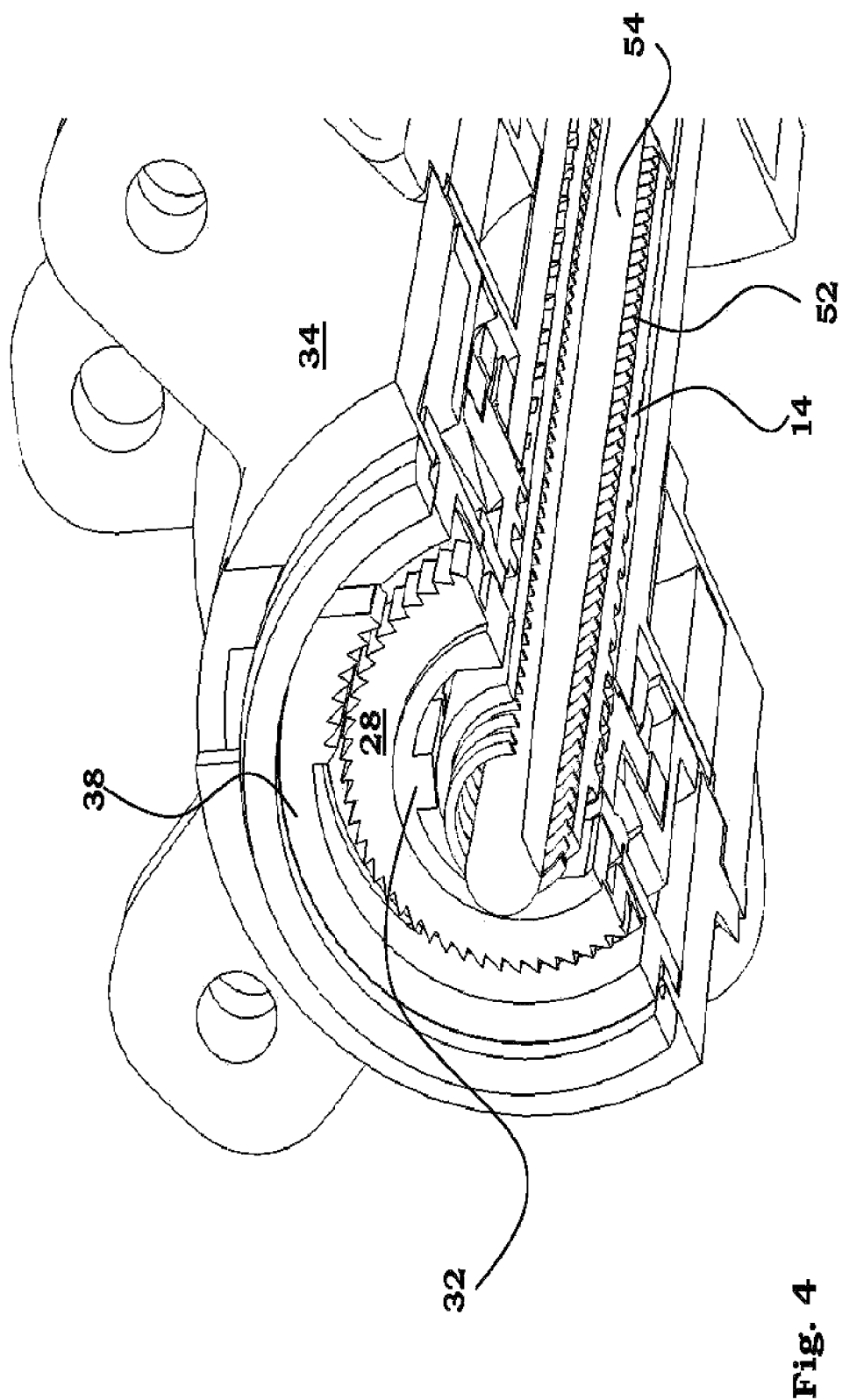
FIG. 4 is a detailed view of the drive part of the embodiment of FIG. 1.

The resilient member 52, hereafter named return spring, which is arranged inside said hollow plunger rod, has a front end resting against an inner wall at the front end of the hollow plunger rod and rear end resting against a fixed point on an inner wall at the distal end of said rear housing. An alternative is that rear end of said return rests against an inner wall inside the drive shaft as seen in FIG. 3. The return spring is prevented from buckling by a pin 54 inside the spring. The function of the return spring will be explained below.

The device is intended to function as follows. Before the first use the auto-injector should be loaded with a medicament container. The container holder 10 is then detached, e.g. screwed off, from the rear housing. The flexible locking means 38 flex radial outwardly releasing its first radial inwardly protruding means from the corresponding first set of grooves on the outer circumference surface of said first locking nut, whereby the first locking nut 28 is unlocked and free to rotate allowing the hollow plunger rod 14 to be extended to its most extended position towards the front end of the device due to the force exerted by the return spring. Because the first locking nut is free to rotate and the resiliency of the return spring, the plunger rod can be resiliently pushed towards the rear end of the device by the stopper of the container when the container holder is attached to the rear housing. The contact between the stopper and the spinner is maintained all the time due to the resiliency of the return spring allowing an automatically adjusting position of the hollow plunger rod in relation to a stopper. The rotation of the plunger rod when it is pushed towards the rear end of the device is facilitated by the spinner 16 at the front end of the plunger rod and being in contact with the stopper.

When the container holder is attached to the rear housing, the first radial inwardly protruding means of the flexible locking means 38 will engage the corresponding first set of grooves on the outer circumference surface of said first locking nut during the final movement of the container holder, because the flexible locking means 38 are forced radially inwards. The first locking nut 28 and thereby the hollow plunger rod are thus locked from rotation.

The next step is to set a proper dose. This is done by turning the dose knob 50. Preferably the dose knob is arranged with some type of indications means that cooperate with corresponding indications means on the rear housing in order to display the set dose. The turning of the dose knob causes the drive shaft 42 to turn, whereby the energy accumulating member 46 is tensioned for accumulating energy, e.g. a torque force. The second radial inwardly protruding means of the flexible engagement means 26 of the drive nut 18 and the second set of grooves circumferentially arranged on the second locking nut 44 comprises a geometry such that the second radial inwardly protruding means of the flexible engagement means 26 may slide over the second set of grooves circumferentially arranged on the second locking nut 44 in only one direction. The drive shaft is prevented from rotating back because the drive nut is in the rotationally locked position, since the first set of engagement means 20 are in contact with the corresponding second set of engagement means 22. When the proper dose has been set, the auto-injector is ready for use.

In case a wrong dose has been set, the dose knob may be displaced axially, e.g. by pulling the dose knob towards the rear end of the device, for resetting the dose, such that the second radial inwardly protruding means of the flexible engagement means 26 of the drive nut 18 come out of engagement from the second set of grooves circumferentially arranged on the second locking nut 44, whereby the energy accumulated in the energy accumulating member 46 will be transferred to the drive shaft 42 allowing the dose knob to be turned back. Thereafter, the dose knob is manually pushed towards the front end of the device or automatically pushed towards the front end of the device by the force of a resilient member (not shown) that may preferably be arranged between an inner wall at the distal end of the rear housing and a wall of the dose knob.

When the auto-injector is ready for use, the patient then penetrates the skin of the injection site. After this the patient actuates the manually activated knob 40, whereby the second set of engagement means 22 of the activating mechanism 24 are brought out of contact with the first set of engagement means 20 of the drive nut. Because the drive shaft is engaged to the drive nut via the engagement between the second radial inwardly protruding means of the flexible engagement means 26 and the second set of grooves of the second locking nut 44, and because of the torque force of the energy accumulating member, the drive shaft and the drive nut are both rotated. Since the first locking nut 28 and the hollow plunger rod are locked from rotation, the threads of the drive nut will now interact with the threads of the hollow plunger rod causing the hollow plunger rod to move axially towards the front end of the device. The axial movement of the hollow plunger rod causes the stopper also to move towards the front end of the device and thus the medicament to be expelled through the injection needle. The injection is completed when the drive shaft has rotated back to its original position.

It is to be understood that the embodiment described above and shown in the drawings is to be regarded only as a non-limiting example of the invention and that it may be modified in many ways within the scope of the patent claims.

The invention claimed is:

1. An auto-injection device having a front end and a rear end and comprising:
   a rear housing and a container housing releasably connected to each other;
   a medicament container disposed within the container housing, wherein the container has a front opening with or for a delivery member for delivering a medicament therethrough and at least one movable stopper;
   a dose setting mechanism configured for setting and resetting a dose of the medicament;
   a drive nut releasably connected to the dose setting mechanism;
   a hollow plunger rod rotatably connected to the drive nut and arranged to have a front end of the hollow plunger rod in contact with the at least one movable stopper;
   an energy accumulating member having a first end connected to the dose setting mechanism and a second end connected to a fix point of the rear housing such that when the dose setting mechanism is operated to set the dose, the energy accumulating member accumulates energy in terms of at least one predetermined step;
   an activating mechanism releasably connected to the drive nut and configured for locking the drive nut against rotation when the dose is being set and for releasing the drive nut when the activating mechanism is manually activated such that the hollow plunger rod is linearly displaced toward the front end of the device by rotation of the drive nut due to the energy accumulated in the energy accumulating member and transferred through the dose setting mechanism; and
   a positioning mechanism operably connected to the hollow plunger rod and configured for locking the hollow plunger rod from being resiliently and axially displaced by rotation, wherein the positioning mechanism comprises a first locking nut rotationally locked but axially slidable surrounding the hollow plunger rod and arranged to co-operate with a flexible locking device arranged on the rear housing for locking the first locking nut from rotation, and a resilient member arranged inside the hollow plunger rod configured for allowing the hollow plunger rod to be resiliently and axially displaced when the first locking nut is unlocked.

2. The auto-injection device of claim 1, wherein the resilient member has a front end resting against an inner wall at the front end of the hollow plunger rod and a rear end resting against a fixed point on an inner wall at a distal end of the rear housing.

3. The auto-injection device of claim 1, wherein the hollow plunger rod comprises elongated grooves on an outer surface of the hollow plunger rod that interface with corresponding protrusions on an inner circumferential surface of the first locking nut, whereby the hollow plunger rod is rotationally locked to the first locking nut but axially slidable through the first locking nut.

4. The auto-injection device of claim 1, wherein the flexible locking device comprises a first radial inwardly protruding device that interfaces with a corresponding first set of grooves on an outer circumferential surface of the first locking nut, such that when the first radial inwardly protruding device is in contact with the corresponding first set of grooves, the first locking nut is rotationally locked.

5. The auto-injection device of claim 1, wherein the drive nut comprises a set of threads on an inner circumference surface of the drive nut that interfaces with a corresponding set of threads on an outer circumferential surface of the hollow plunger rod.

6. The auto-injection device of claim 1, wherein the drive nut further comprises a flexible engagement device that extends through a recess on an outer circumferential surface of the drive nut, and the flexible engagement device comprises a second radial inwardly protruding device.

7. The auto-injection device of claim 6, wherein the dose setting mechanism comprises a dose knob, a drive shaft operatively connected to the dose knob, and a second locking nut attached to a front end of the drive shaft; the second locking nut comprises a second set of grooves on an outer circumferential surface of the second locking nut that interfaces with the second radial inwardly protruding device; and the second set of grooves and the second radial inwardly protruding device have a geometry such that when the dose is set, the drive shaft is rotated in only one direction.

8. The auto-injection device of claim 7, wherein the first end of the energy accumulating member is connected to the drive shaft.

9. The auto-injection device of claim 8, wherein the drive nut further comprises a first set of engagement devices on the outer circumferential surface of the drive nut that interfaces with a corresponding second set of engagement devices on an inner circumferential surface of the activating mechanism, such that the first and second sets of engagement devices are arranged to be in contact with each other for locking the drive nut in a rotationally locked position when the energy accumulating member is tensioned via the drive shaft for accumulating the energy.

10. The auto-injection device of claim 9, wherein the activating mechanism comprises a manually activated knob, such that when the manually activated knob is actuated, the second set of engagement devices is released from the first set of engagement devices, whereby the energy accumulated in the energy accumulating member is transferred to the drive nut via the drive shaft and the second locking nut for allowing the drive nut to rotate and thereby allowing the hollow plunger rod to be axially driven towards the front end of the device.

11. The auto-injection device of claim 10, wherein the dose knob and the drive shaft are arranged to be axially displaced, such that the second set of grooves of the second locking nut and the second radial inwardly protruding device of the flexible engagement device are forced out of engagement for resetting the dose.

* * * * *